(12) United States Patent
Lo

(10) Patent No.: US 6,892,574 B1
(45) Date of Patent: May 17, 2005

(54) FOOT PRESSURE TESTING STRUCTURE

(76) Inventor: Ming-Jor Lo, 11F-4, No. 197 Nanking East Road Sec. 4, Taipei (TW)

( * ) Notice: Subject to any disclaimer, the term of this patent is extended or adjusted under 35 U.S.C. 154(b) by 0 days.

(21) Appl. No.: 10/902,166

(22) Filed: Jul. 30, 2004

(51) Int. Cl.$^7$ .............................................. A63B 5/22
(52) U.S. Cl. .................. 73/379.01; 36/44; 33/515; 602/10
(58) Field of Search ........................... 73/172, 379.01; 36/44; 33/515; 602/210

(56) References Cited

U.S. PATENT DOCUMENTS

| | | | |
|---|---|---|---|
| RE32,698 E | * | 6/1988 | Brown ........................... 36/44 |
| 4,906,425 A | * | 3/1990 | Poussou ...................... 264/102 |
| 5,797,862 A | * | 8/1998 | Lamont ........................ 602/10 |
| 6,493,958 B1 | * | 12/2002 | Tadin ........................... 33/515 |
| 6,625,897 B2 | * | 9/2003 | Tadin ........................... 33/515 |

* cited by examiner

Primary Examiner—Edward Lefkowitz
Assistant Examiner—Jewel V. Thompson

(74) Attorney, Agent, or Firm—Rosenberg, Klein & Lee

(57) ABSTRACT

An improved foot pressure testing structure which comprises a test memory mold plate, a meshed plate and an evenly distributed convex moldboard being stacked with each other on a sole, such that when a patient wears the foot pressure testing structure and walks several steps (or for several minutes) for a test, the test memory mold plate is pressed due to the weight and pressure produced by the patient and the time accumulated in such walking activity, which causes the bottom of the test memory mold plate to be attached closely to and embedded deeply into the meshed plate and the moldboard to form a concave line. The length, depth, area of distribution, and variation of density of the concave line varies with different gaits, and such information can be used as a reference for medical or athletic evaluators to analyze the position and magnitude of the exerted force and the central line of the pressure along a traveling path to facilitate the medical assessment and production of a foot accessory such as a foot base and a pair of shoes. The foot pressure testing structure according to the invention has the features of simple structure, low cost, easy-to-operate, and visually inspecting the result without requiring any other additional measuring instruments.

1 Claim, 4 Drawing Sheets

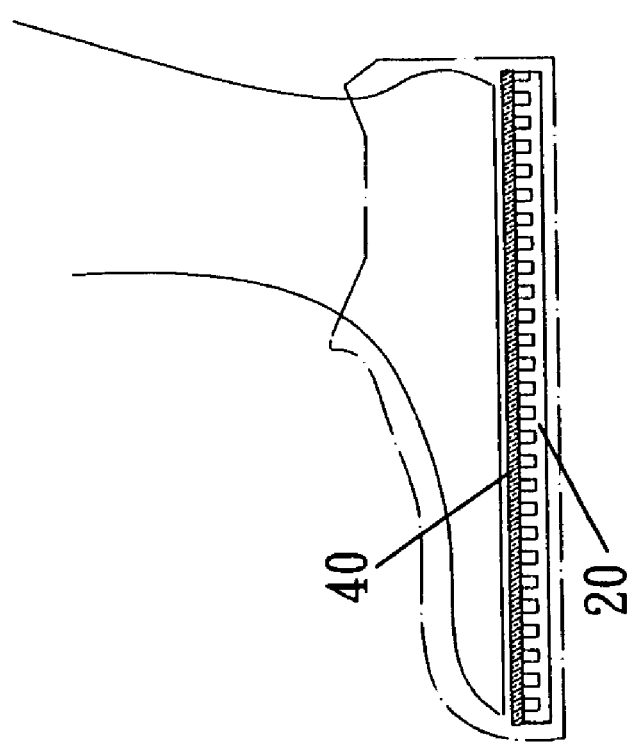
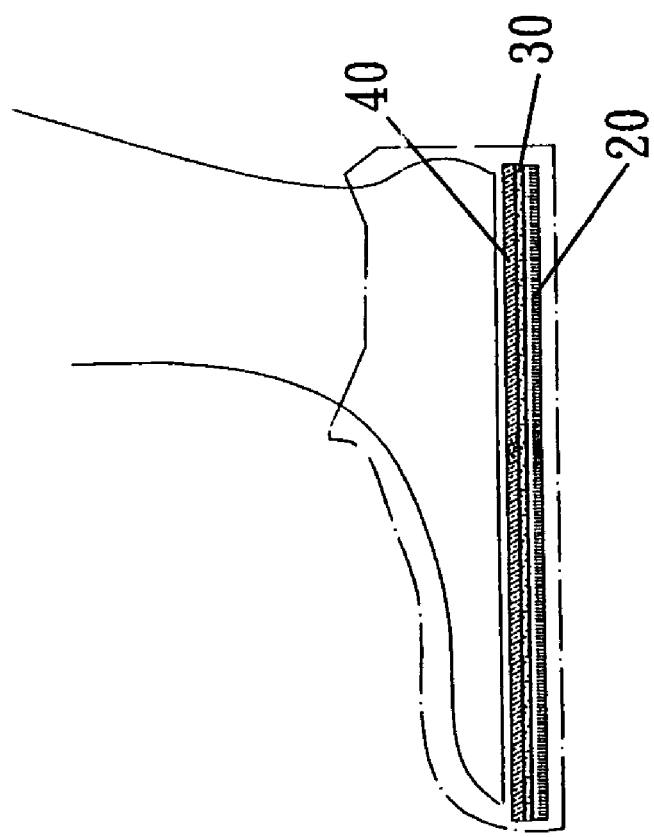

FOOT PRESSURE TESTING STRUCTURE

BACKGROUND OF THE INVENTION

1. Field of the Invention

The present invention relates to an improved foot pressure testing structure, more particularly to an improved foot pressure testing structure that makes use of a footprint mat method to movably mold the magnitude and the central line of a traveling path of the pressure exerted on our feet as a reference for the medical assessment and production of foot accessories such as foot-bases and shoes.

2. Description of the Related Art

Feet play an important role for supporting our body weight, reducing the force exerted on our lower limbs and related joints, absorbing vibrations, buffering impacts and controlling the balance of our body when our body is in contact with the ground. Such functions can be carried out mainly by the coordination of our tissues including bones, ligaments and muscles, etc.

In general, at least 80% of us have foot problems, and injuries to our ankles or feet change the dynamics of our gait and further produce pressure on the joints of our lower limbs, and thus may cause pathological changes to our joints. However, such problems usually can be corrected by appropriate assessments, treatments and medical care.

In fact, the study of foot pressure started at the end of the $19^{th}$ Century, sand, gypsum and paper and ink were used for observations at early stage. Later, Harris and Beath invented the foot print mat based on Morton's kinetograph and made use of a static standing pose and the principle of the grids of different depths and ink to obtain a foot pressure diagram.

The present gait assessment is a traditional and effective foot assessment. However, the gait assessment requires some techniques and takes a long-time practice as well as having a standardization of the process before a medical professional to develop the necessary assessing skill. The method of analyzing the gait relates to a foot pressure testing equipment that mainly combines a force platform 10 (for the patient to take a test by stepping on this platform) as shown in FIG. 1 or a sole force testing platform (not labeled in the figure) which is a sole using a measuring platform to be placed at the sole of a pair of shoes, such that a patient wears such shoes to take the test and measure the ground reaction forces while the patient is walking.

The foot pressure analysis in a gait assessment is used to study and compare the change of foot pressure caused by different sports or diseases and compare the effects before and after the treatments by foot accessories. At present, the foot pressure measuring instruments have the following three situations:

(1) Since the existing foot pressure measuring instruments are imported, therefore the price is high, and the costs for consuming materials and maintenance are also high.
(2) The functions of the current foot pressure measuring instruments are complicated, and it is not easy for a non-professional to operate such an instrument for analysis.
(3) It is not easy to quickly and accurately assess the foot pressure situation of the shoes while the tester is walking.
  a) Since the precision of the sensor of an insole type measuring system is affected by high temperature and humidity, therefore it is necessary to repeat the test many times and get the average.
  b) The insole type measuring system also may have errors on measuring the foot pressure due to the pressure formed by the curved surface of the insole itself and the sensor may be damaged easily by the repeated exertion of pressure.

In view of the foregoing shortcomings, the inventor of the present invention based years of experience in the related field to conduct extensive researches and experiments and finally invented an improved structure to reduce costs and simplify the operation of the instrument.

To make it easier for our examiner to understand the objective of the invention, its structure, innovative features and performance, we use a preferred embodiment together with the attached drawings for the detailed description of the invention.

SUMMARY OF THE INVENTION

This present invention discloses an improved foot pressure testing structure, which comprises a test memory mold plate, a meshed plate and an evenly distributed convex moldboard being stacked with each other on a sole, such that when a patient wears the foot pressure testing structure and walks several steps (or for several minutes) for a test, the test memory mold plate is pressed due to the weight and pressure produced by the patient and the time accumulated in such walking activity, which causes the bottom of the test memory mold plate to be attached closely to and embedded deeply into the meshed plate and the moldboard to form a concave line. The length, depth, area of distribution, and variation of density of the concave line varies with different gaits, and such that information can be used as a reference for medical and sport professionals can make use of the different conditions of the gait and the magnitude of the exerted force on the feet while a patient is walking to analyze the position of a patient's bad foot, the magnitude of exerted forces, and the path of the pressure along the central line of traveling and facilitate the medical assessment and production of the foot accessories such as insoles and shoes. The foot pressure testing structure of the present invention is simple, low-cost, and easy-to-operate and requires no other measuring instruments but only requires visual inspection for the test result.

BRIEF DESCRIPTION OF THE DRAWINGS

FIG. 3 is an illustrative view of the foot pressure testing instrument being placed at the sole for a patient to wear according to the present invention.

FIG. 3A is an illustrative view of the foot pressure testing instrument being placed at the sole for a patient to wear according to another preferred embodiment of the present invention.

DETAILED DESCRIPTION OF THE PREFERRED EMBODIMENTS

Figure 1:
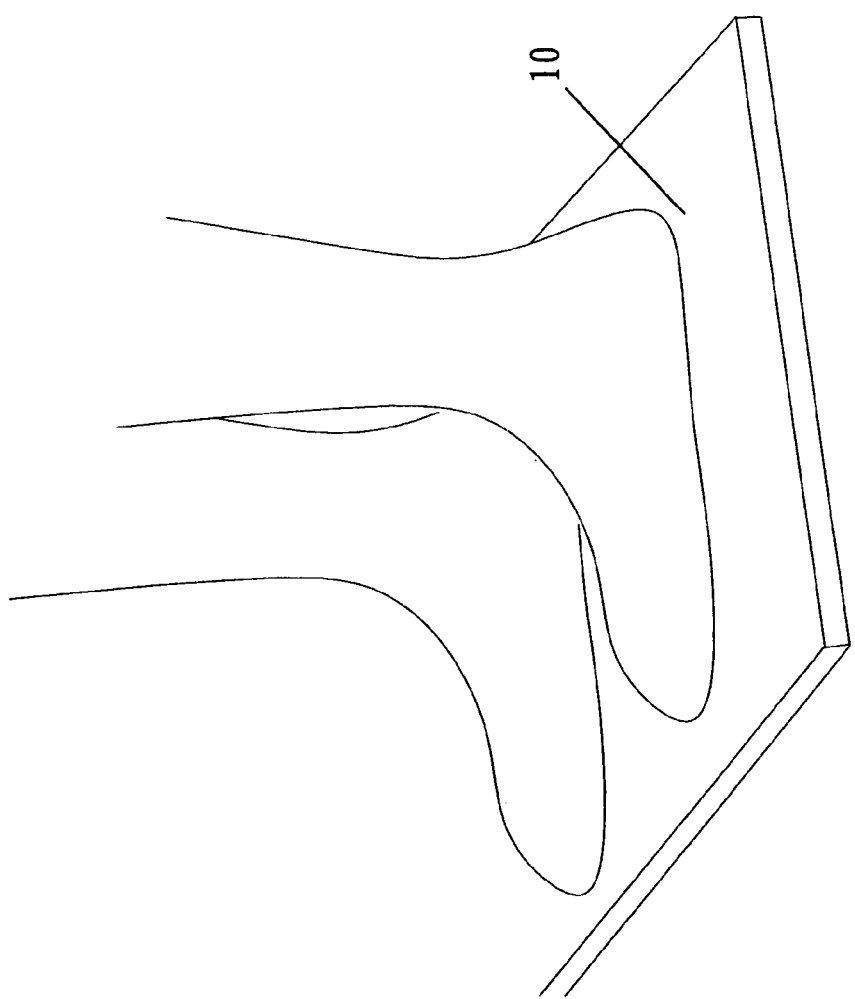
FIG. 1 is an illustrative view of a prior-art foot pressure testing instrument using a force board for the test according to the prior art.

Please refer to FIG. 1 for an illustrative view of the prior-art foot pressure measuring instrument using a force board for the test. Its method, objectives and shortcomings have been described in the previous section and thus will not be described here.

Figure 2A:
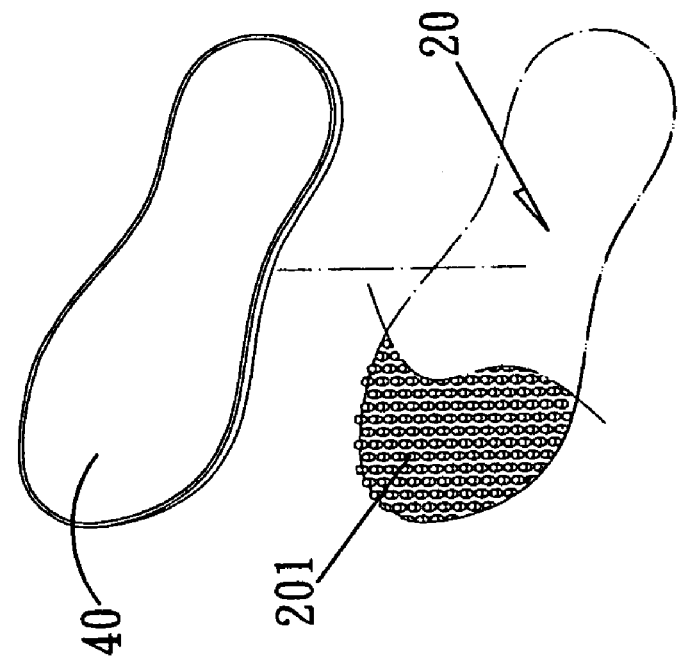
FIG. 2A is a perspective view of another preferred embodiment of the present invention.
Figure 2:
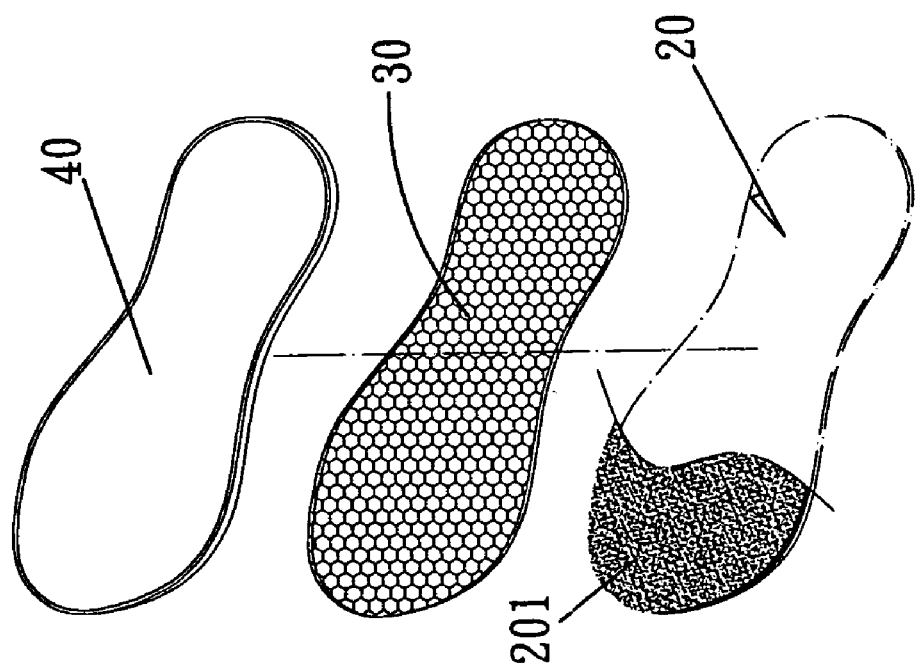
FIG. 2 is a perspective view of the present invention.
Figure 4:
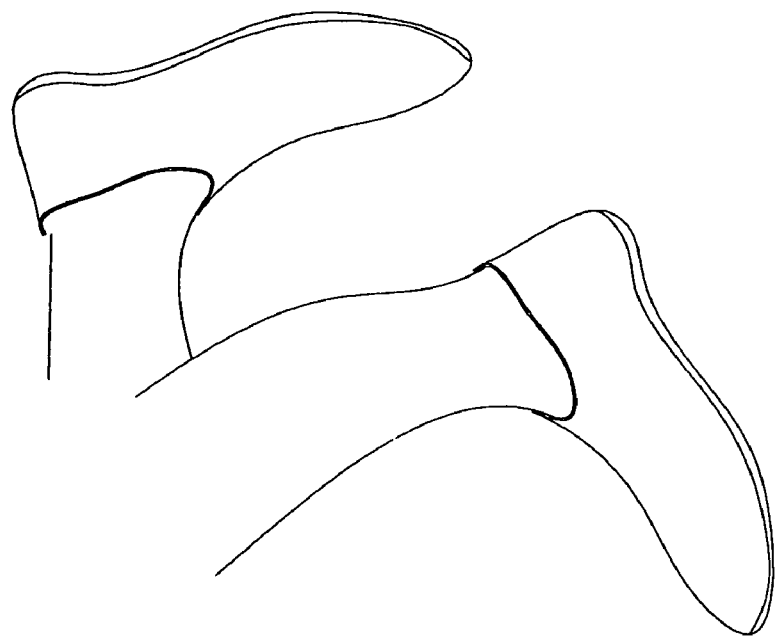
FIG. 4 is an illustrative view of performing the test while a patient is walking according to the present invention.
Figure 5:
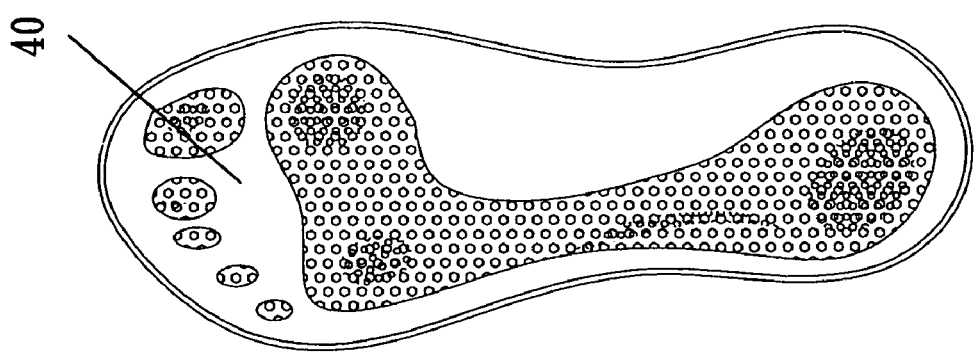
FIG. 5 is an illustrative view of the concave lines formed on the gait assessing bottom of the testing memory plate according to the present invention.
Figure 5A:
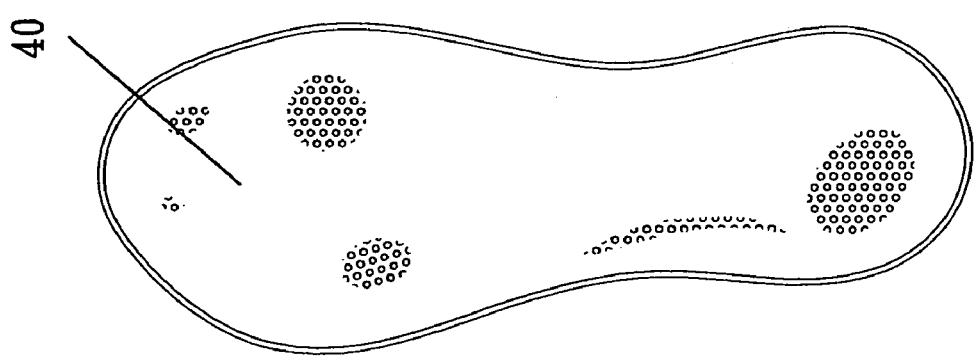
FIG. 5A is an illustrative view of the protruded lines formed on the gait assessing top of the testing memory plate according to the present invention.

The present invention discloses an improved foot pressure testing structure, which comprises:

- a moldboard 20, being a flexible sole (as shown in FIGS. 2 and 2A) and having a plurality of protrusions 201 thereon, wherein the shape, size, coarseness, and density of distribution of the protrusions 201 vary as needed, and a meshed plate 30 being coupled on top of the moldboard 20; and
- a testing memory plate 40, being a foam flexible member made of a memory material in the shape of an insole and having the features of being easily compressed and deformed, durable and permanently fixed into a shape after being deformed;
- thereby, the moldboard 20 and the testing memory plate 40 (as shown in FIGS. 2A and 3A) are stacked on the sole or a meshed plate 30 (as shown in FIGS. 2 and 3) is installed between the moldboard 20 and the testing memory plate 40 for a patient (as shown in FIG. 4) to walk several steps (or several minutes), and then the bottom of the testing memory plate 40 is compressed to attach closely with and sinks into the protrusions 201 of the moldboard 20 to form a concave line. After the testing memory plate 40 is removed (as shown in FIG. 5), the size, depth, shape, variation of density of the concave line are used to cross reference with the depth and clarity of the protruded lines on the front side of the testing memory plate 40 (as shown in FIG. 5-A) to determine the distribution and magnitude of a foot pressure (the protruded lines are the lines produced when the testing memory plate 40 measures the foot pressure, the bottom of the testing memory plate 40 is pressed by the protrusions 201 of the moldboard 20, and the points and areas with a larger force exerted form the protruded lines on the front side of the testing memory plate 40) and analyze and assess a bad force exertion position, a magnitude of force exertion and a traveling path of pressure along the central line of a patient's walk to facilitate a medical assessment and a production of foot accessories such as insoles and shoes.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What the invention claimed is:

1. An improved foot pressure testing structure, comprising:
    a moldboard, being a flexible sole and having a plurality of protrusions thereon, wherein the shape, size, coarseness, and density of distribution of said protrusions vary as needed, and a meshed plate being coupled on top of said moldboard; and
    a testing memory plate, being a foam flexible member made of a memory material in the shape of an insole and having the features of being easily compressed and deformed, durable and permanently fixed into a shape after being deformed;
    thereby, said moldboard and said testing memory plate are stacked on said sole and a meshed plate is installed between said moldboard and said testing memory plate for a patient to walk selectively for a plurality of steps and a plurality of minutes, and then the bottom of said testing memory plate is compressed to attach closely with and sinks into said protrusions to form a concave line, and the size, depth, shape, variation of density of said concave line are used to cross reference with the depth and clarity of the protruded lines on the front side of said testing memory plate to determine the distribution and magnitude of a foot pressure and analyze and assess a bad force exertion position, a magnitude of force exertion and a traveling path of pressure along the central line of a patent's walk to facilitate a medical assessment and a production of foot accessories such as insoles and shoes.

* * * * *